(12) United States Patent
Policello et al.

(10) Patent No.: US 6,197,876 B1
(45) Date of Patent: Mar. 6, 2001

(54) HETEROCYCLIC AMINE MODIFIED SILOXANES

(75) Inventors: George A. Policello, Ossining; Gerald J. Murphy, Hopewell Junction, both of NY (US)

(73) Assignee: CK Witco Corporation, Greennwich, CT (US)

( * ) Notice: Subject to any disclaimer, the term of this patent is extended or adjusted under 35 U.S.C. 154(b) by 0 days.

(21) Appl. No.: 09/257,150

(22) Filed: Feb. 24, 1999

(51) Int. Cl.$^7$ .......................... C08L 83/08; C08G 77/26; A01N 33/02

(52) U.S. Cl. .................... 524/588; 524/189; 524/190; 524/211; 524/214; 524/261; 524/285; 524/287; 524/612; 528/27; 528/28; 528/33; 528/38; 504/104; 504/209; 252/357; 71/DIG. 1

(58) Field of Search .................... 504/116, 104, 504/105, 106, 108, 124, 130, 136, 139, 193, 209, 214, 223, 206; 71/DIG. 1; 528/27, 28, 33, 38; 524/211, 189, 190, 214, 287, 285, 588, 261, 612; 516/55, 77, 198; 424/407; 252/351, 357

(56) References Cited

U.S. PATENT DOCUMENTS

| | | | |
|---|---|---|---|
| 3,389,160 | 6/1968 | Reid | 260/448.2 |
| 4,018,723 | * 4/1977 | Kanner et al. . | |
| 4,728,690 | * 3/1988 | Lammerting et al. | 524/714 |
| 4,946,880 | * 8/1990 | Costanzi et al. | 524/96 |
| 4,973,352 | 11/1990 | Heinrich | 71/91 |
| 5,104,647 | 4/1992 | Policello | 514/772 |
| 5,360,571 | 11/1994 | Kilgour | 252/174 |
| 5,504,054 | 4/1996 | Policello | 504/116 |
| 5,558,806 | 9/1996 | Policello | 252/355 |
| 5,561,099 | 10/1996 | Murphy | 504/116 |
| 5,612,409 | * 3/1997 | Chrobaczek et al. | 524/838 |
| 5,658,851 | 8/1997 | Murphy | 504/116 |
| 5,891,977 | 4/1999 | Dietz et al. . | |
| 5,998,331 | 12/1999 | Policello | 504/116 |

FOREIGN PATENT DOCUMENTS

| | | |
|---|---|---|
| 4318536 | 12/1994 | (DE) . |
| 4318537 | 12/1994 | (DE) . |
| 0112593 | 7/1984 | (EP) . |
| 0483095 | 4/1992 | (EP) . |
| 535596 | 7/1993 | (EP) . |
| 791384 | 8/1997 | (EP) . |
| 8912394 | 12/1989 | (WO) . |
| 94/29324 | 12/1994 | (WO) . |
| 9723281 | 7/1997 | (WO) . |
| 9732475 | 9/1997 | (WO) . |

OTHER PUBLICATIONS

Chemical Abstract—84:43919.
Chemical Abstract—101:67823.
Chemical Abstract—99:83744.
Chemical Abstract—97:74345.
Chemical Abstract—124:258947.
Stevens, PJ, "Organosilicone Surfactants as Adjuvants for Agrochemicals" Pesticide Science, vol. 38, No. 2/03 (Jan. 1, 1993).
Chemical Abstract—52503–47–6.
Chemical Abstract—106:191231.
Chemical Abstract—106:80405.
Chemical Abstract—103:89334.
Chemical Abstract—103:66794.
Chemical Abstract—101:224838.
Sandbrink et al., *Pest Sci.* 38: 272–273 (1993).
Gaskin et al., *Pest Sci.* 38: 185–192 (1993).
Snow, *Langmuir* 9: 424–430 (1993).
Okahama et al., *Synthetic Communications*, 15(7): 649–655 (1985).
Bogdan et al., *Comprehensive Handbook on Hydrosilyation*, Pergamon Press, 122–123 and 558–568.
Gaskin et al., *Pest Sci* 38: 192–200 (1993).
Silicon–Modified Carbohydrate Surfactants II: Siloxanyl Moieties Containing Branched Structures (1996).

* cited by examiner

*Primary Examiner*—Robert Dawson
*Assistant Examiner*—Jeffrey B. Robertson
(74) *Attorney, Agent, or Firm*—Shirley S. Ma, Esq.

(57) ABSTRACT

The present invention teaches heterocyclic amine modified siloxanes and their use, a preferred of which is as adjuvants for pesticides. The heterocyclic amine modified siloxanes have siloxane backbones with pendant, terminal or intermediate heterocyclic amine groups, which may contain one or more heteroatoms, i.e., nitrogen, sulfur or oxygen. The heterocyclic amine groups or the siloxane may be functionalized further with alkyl or alkyleneoxide groups.

21 Claims, No Drawings

HETEROCYCLIC AMINE MODIFIED SILOXANES

BACKGROUND OF THE INVENTION

Many herbicides require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, or to provide penetration of the herbicide into the plant cuticle. These adjuvants are provided either as a tankside additive or used as a component in herbicide formulations.

Gaskin, et al., (*Pestic. Sci.* 1993, 38, 185–192) demonstrated that some trisiloxane ethoxylates (TSE), such as Silwet L-776® surfactant (available from Witco Corp. of Greenwich, Conn.), can antagonize cuticular penetration of a herbicide into grasses, when compared to the herbicide alone. The term antagonism is used to indicate that the treatment of herbicide plus adjuvant is less effective than the comparative herbicide treatment.

Sandbrink, et al., (*Pest. Sci.* 1993, 38, 272–273) published that a TSE antagonized glyphosate performance relative to glyphosate alone in the control of *Panicum maximum*. Jacq. Snow, et. al., Langmuir, 1993, 9, 424–30, discusses the physical properties and synthesis of novel cationic siloxane surfactants. These siloxanes are based on the reaction of a chloropropyl modified trisiloxane with an alkanolamine, such as N-methylehanolamine, which was further reacted with a halide to make a quaternary surfactant.

Petroff, et al., (EP 92116658) describes the use of cationic, quaternary trisiloxanes to enhance the efficacy of glyphosate on velvetleaf, a broadleaf weed. Henning, et al., (DE4318537) describes cationic siloxanyl modified polyhydroxy hydrocarbon or carbohydrate for use with plant protection agents. These compounds are derived from a saccharide containing 1 to 10 pentose and/or hexose units, modified with a quaternary ammonium group, and a siloxane moiety. Reid, et al., (U.S. Pat. No. 3,389,160) describes amino modified siloxane alkoxylates where the amino functionality appears as the terminal group on the alkyleneoxide moiety, opposite the siloxane group. Policello in PCT WO 97/32475 discloses amino modified siloxanes wherein the amine is bound by an ether bond to the siloxane backbone wherein the amine may be terminal or pendant to the backbone.

Kilgour and Petty in U.S. Pat. No. 4,526,996 disclose the manufacture of heterocyclic modified monomeric silanes, but the utility of such silanes is as cross linkers, not as intermediates for any further silicone compounds. Czech in U.S. Pat. No. 5,8087,956 discloses the use of amino/epoxide/siloxane polymers, referred to as amino [AB]n polymers, but the amines therein are generally linear in nature, not cyclic.

SUMMARY OF THE INVENTION

The present invention teaches heterocyclic amine substituted siloxanes, known henceforth as heterocyclic amino modified siloxanes, and their use, a preferred of which is as adjuvants for pesticides. The heterocyclic amine modified siloxanes have siloxane backbones with pendant, terminal or intermediate heterocyclic amine groups, which may contain one or more heteroatoms.

Optionally, the heterocyclic amine modified siloxanes of this invention may be blended with conventional trisiloxane alkoxylates (TSAs). Blends of these amino containing siloxanes with TSAs provide superspreading properties on difficult to wet surfaces. Moreover, these amine modified siloxanes may be blended with organic surfactants, as emulsifiers, dispersants or cosurfactants.

HETEROCYCLIC AMINE MODIFIED SILOXANES

The heterocyclic amine modified siloxanes of the present invention are siloxanes, i.e., compounds with at least one Si-PSi bond, which have at least one heterocyclic amine attached to the silicon through an Si-C bond. A heterocyclic amine is a cyclic group of at least four carbon atoms and containing at least one nitrogen atom. The ring may contain one oxygen or sulfur atom or up to two additional nitrogen atoms and said heterocyclic group may have further substituents thereon, such as alkyls, hydroxyl and polyethers. In one preferred embodiment these substituents are on the additional nitrogen(s) in the ring. The heterocyclic ring should be fully saturated, though external substituents thereon may have unsaturated functionalities.

Preferably, the heterocyclic amine modified siloxanes of the present invention have the average general formula:

$$[SiO_{4/2}]_d[MeSiO_{3/2}]_e[O_{1/2}MeSi(Q)O_{1/2}]_f[O_{1/2}SiMe_2Q]_g$$

wherein f is between 0 to 50, preferably 1 to 5, more preferably 1 to 2, most preferably 1, d=0 to 2, most preferably 0, e=0 to 3, most preferably 0, g is, if the siloxane is not cyclic, 2+e+2d, or zero if the siloxane is cyclic, d+e+f+g=2 to 50, Q is either $B(O)_j(C_aH_{2a}O)_bRV$ or $R^1$, each a is 2 to 4, preferably 2 to 3, each b is 0 to 15, preferably 0 to 8, B is a divalent bridging group of C1 to C6, preferably C3 to C4, R is a divalent organic group containing 2 to 8 carbons, preferably 3 to 4 carbons, each optionally OH substituted, $R^1$ is either a polyether or an alkyl radical containing 1 to 18 carbons, preferably methyl, j=0 or 1, preferably 1, at least one Q is not $R^1$, and V is a heterocyclic amine monovalent radical of the formula, $-NC_pH_pR^2_p(NR^2)_x$, or $-NC_pH_pR^2M_r$, where p=4 to 8, preferably 4 to 5, z=0 to 3, preferably 1, r=0 to 3, preferably 1, $R^2$ is hydrogen, a univalent organic group containing 1 to 4 carbons, or $-(C_aH_{2a}O)_nR^3$, where h=1 to 8, preferably 1 to 3, $R^3$ is hydrogen, an alkyl group of 1 to 4 carbons, or acetyl, and M=oxygen or sulfur.

Additionally the heterocyclic amine modified siloxane compositions of the present invention may have intermediate units of the heterocyclic amine, i.e., alternating units of polysiloxane $[XSiO(R^1)_2X]_c$ and a heterocyclic diamine of the general structure $[-NC_pH_pR^2_pN-]$ wherein c=1 to 30, more preferably c=1 to 15, X is $-B(O)_j(C_aH_{2a}O)_bR-$ as defined above. Preferably such structures are of 1 to 100 repeating units, more preferably 1 to 30. It is noted that the ends of these polymers would be dependent on the chain terminator used in the reaction. These copolymers may be referred to as amino $[AB]_n$ copolymers.

Exemplary such structures are

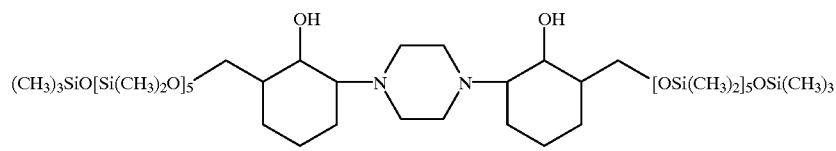

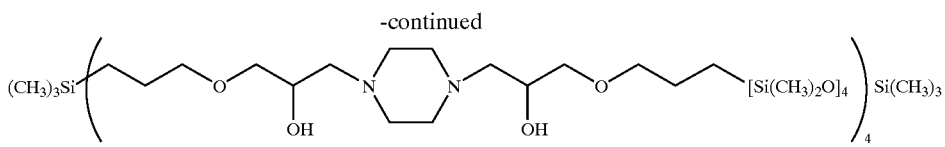

Preferably a is such that there is a mixture of ethylene oxide (EO), propylene oxide (PO) units or butylene oxide (BO), where a=2 to 4. Preferably, for aqueous applications, there is a preponderance of EO units, most preferably every a=2. For non-aqueous applications, such as crop oil concentrates, there may be more PO and BO units. When Q contains a mixture of oxyalkylenes, it may be blocked or random. One skilled in the art will understand the advantages in the position of the oxyethylene relative to the oxypropylene, when the alkyleneoxide group is blocked.

Preferably most $R^1$ groups are methyl, but some may be polyethers of the structure —$(C_aH_{2a}O)_hR^3$ as defined above. Exemplary B are —$(CH_2)_2$—, —$(CH_2)_3$—, and —$CH_2CH(OH)CH_2$—. Exemplary R groups are —$(CH_2)_2$—, —$(CH_2)_3$—, —$CH_2CH(OH)CH_2$— and —$CH_2C_6H_9(OH)CH_2$—. Examples of $R^2$ are —$CH_3$, —$C_2H_5$, —$C_2H_2OH$, $(C_2H_4O)_3(C_3H_6O)_2H$; —$(C_2H_4O)_2CH_3$; and —$(C_3H_6O)_3OH$.

Some examples of V are —$NC_4H_8$, —$NC_4H_8O$, —$NC_4H_8S$, —$NC_5H_{10}$, —$NC_4H_8NH$, —$NC_4H_7(CH_3)$; —$NC_4H_8NC_3H_6OH$; and —$NC_4H_8N(C_2H_4O)_2OH$.

The Q groups may include protonated amines, i.e, where there is a hydrogen ion attached to the nitrogen in the Q group, which can occur to the heterocyclic amine modified siloxanes under acidic conditions. Also contemplated herein are quaternary versions of Q, i.e., where there is a fourth group on the nitrogen in Q consisting essentially of an alkyl group containing 1 to 4 carbons, but said quaternary compounds are not preferred for use since they would tend to be phytotoxic.

Preferred Q structures are wherein B is a 3 carbon, alkylene groups, a=2, b 0 to 4, R is a 3 carbon alkylene group, V=$NC_pH_{2p}(NR^2)_z$, p=4, z=1, $R^2$=$(CH_2CH_2O)_hR^3$, h=1–2, $R^3$=hydrogen. Specific Q groups are —$C_3H_6O$ $[C_2H_4O]_4CH_2CH(OH)CH_2NC_4H_8NCH_2CH_2OH$; —$C_3H_6O$ $[C_2H_4O]_4[C_3H_6O]_2CH_2CH(OH)CH_2NC_4H_8N[CH_2CH_2O]_2H$; —$C_3H_6OCH_2CH(OH)CH_2NC_4H_8N[CH_2CH_2O]_2H$; —$C_3H_6O[C_2H_4O]_4CH_2CH(OH)CH_2NC_4H_8O$; and —$C_3H_6OCH_2CH(OH)CH_2NC_4H_8O$. Some Structures representative of Q are as follows:

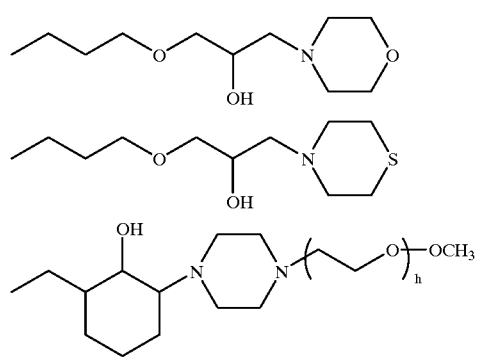

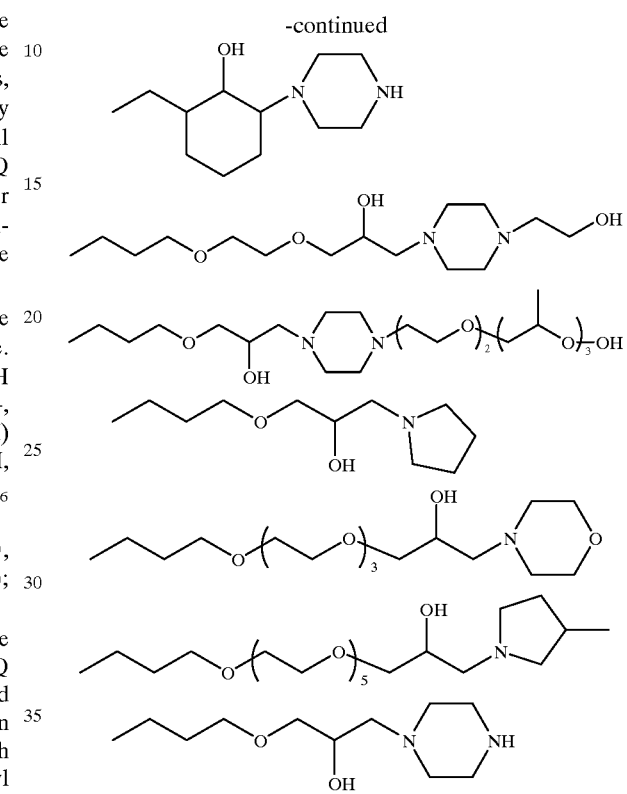

OTHER SILOXANES

In addition the compositions of the present invention optionally may include TSAs of the general formula:

$R^4Me_2SiO[MeSi(G)O]_xSiMeR^4$ wherein x=0 to 2, preferably 1, G=$C_nH_{2n}O(C_2H_4O)_t(C_3H_6O)_wR^5$, n=2 to 4, preferably 3, t=3 to 12, preferably 4 to 8, w=0 to 8, providing that when w is >0, (t+w) is preferably between 5 and 12. $R^5$ is hydrogen, acetyl or a hydrocarbon radical between 1 and 4 carbon atoms. $R^4$ is G, or an alkyl of one to four carbons. The preferred nonionic siloxane alkoxylates are trisiloxane alkoxylates, where x=1, n=3, t=4 to 8, w=0, $R^4$ is Me, $R^5$ is H or Me.

PESTICIDES

The compositions of the present invention also optionally include pesticides, especially acid functionalized ones, i.e., compounds that contain at least one carboxylic, sulfonic or phosphonic acid group or their salt or ester. The term pesticide means any compound used to destroy pests, e.g., rodenticides, fungicides, and herbicides. Illustrative examples of pesticides which can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

EXCIPIENTS

The compositions also may include fatty acid esters, e.g., methyl soyate, for crop oil concentrate formulations, as well as water, for aqueous applications. Buffers, preservatives and other standard excipients known in the art also may be included in the composition. When the compositions of the present are insoluble in distilled water, spreading may be achieved by the addition of a small amount of an acid, such as acetic acid, to protonate the amine functionality, thereby increasing water solubility. Moreover, other cosurfactants, which have short chain hydrophobes which do not interfere with superspreading may be included. See U.S. Pat. No. 5,558,806 to Policello et al., which is incorporated by reference.

MANUFACTURE

The heterocyclic amine modified siloxanes of the present invention may be made by the hydrosilation of a hydridosiloxane with an epoxy intermediate, such as allyl glycidal ether, vinyl cyclohexene monoxide, or an epoxy terminated allyl polyalkyleneoxide, followed by ring opening the epoxide with the appropriate heterocyclic organic amine. The hydridosiloxanes described are commercially available and may be made as known in the art. Hydrosilation conditions depend on the amine and siloxane, but are within the general conditions taught in Marciniec (Marciniec, Bogdan (ed.). *Comprehensive Handbook on Hydrosilylation,* Pergamon Press, pgs. 411 and 412).

Alternatively an epoxy terminated allyl polyalkyleneoxide may be hydrosilated onto a hydridosiloxane backbone and then the epoxide is ring opened with the desired amine. Epoxy terminated, allyl polyethyleneoxide can be prepared by the method outlined by Xue-Ping Gu, et al, (Synthesis of Glycol Diglycidyl Ethers Using Phase-Transfer Catalysis; in *Synthesis Communications June/July* 1985, p. 649–651) from an epoxide and commercially available allyl started polyalkylene oxides.

Alternatively one may start from the reaction product of an allyl chloride and a heterocyclic amine compound and hydrosilate this allylic heterocyclic amine onto hydridosiloxanes.

Yet another method of manufacture would involve the formation of an alkyl dialkoxy heterocyclic amino silane acording to U.S. Pat. No. 4,526,996 to Kilgour and Petty which is incorporated herein by reference. Such alkoxy silanes then can be equilibrated into a linear siloxane or with cyclic tetra and penta dimethylsiloxanes.

To manufacture the amino [AB]n copolymer, the procedures used in U.S. Pat. No. 5,807,956 to Czech may be used, which is incorporated herein by reference, except that the starting amine would be piperzine or a substituted or alkoxylated piperzine.

The heterocyclic amines may be commercially available, e.g., morpholino, piperzine or 1-(2-hydroxyethyl) piperazine, but polyalkylene oxide modified or substituted versions thereof may be manufactured as known in the art.

USE

The heterocyclic amine modified siloxanes may be used in agricultural applications as adjuvants for pesticides wherein the siloxane is applied in a pesticide formulation to agricultural products. The composition of the present invention is useful as a tank side additive, or as a component in a herbicide formulation. In addition the compositions of the present invention are useful as adjuvants for other pesticides, such as, fungicides, insecticides, plant growth regulators, acaracides and the like. The pesticide formulations may be wet, dry, slurries or other formulations as are known in the art.

The siloxanes are added directly to a spray tank along with an acid functional pesticide, or as part of a pesticide formulation. When used as a tankside additive, the siloxane is present at weight concentrations between 0.001% and 5.0%, preferably between 0.025% and 0.5%. Likewise, when the heterocyclic amine modified siloxanes are used in a pesticide formulation (In-can), they are present at weight concentrations that will deliver between 0.001% and 5.0% to the final use dilution, preferably between 0.025% and 0.5%, of the final use dilution.

It is noted that most dilutions will be made with water, but in the case of crop oil concentrates, oils (mineral, silicone, animal or vegetable oils) will be the diluents.

When the compositions of the present invention are used in conjunction with a TSA, the weight ratio of the TSA to the heterocyclic amine modified siloxanes is between 5:95 and 95:5, preferably between 5:95 and 40:60. The blend may be accomplished by mixing physically the two components prior to use, or by adding them separately to a spray mixture at the point of use.

DETAILED DESCRIPTION OF THE INVENTION

The heterocyclic amine modified siloxanes are useful in overcoming the antagonistic effects on pesticide efficacy associated with superspreading, TSAs. Mixtures of the heterocyclic amine modified siloxanes with TSAs provide enhanced spreading properties relative to the individual components alone. In addition, these products provide a low aqueous surface tension (≦25 mN/m at 0.1 wt %), which is desirable for enhanced spreading of pesticide solutions.

When the compositions of the present invention are used in conjunction with nonsilicone surfactants, the weight ratio of the nonsilicone surfactant to the heterocyclic amine modified siloxanes is between 1:99 and 99:1, preferably between 99:1 and 40:60.

The heterocyclic amine modified siloxanes also may be used generally as surface active agents in aqueous formulation where there is an acid functionalized component. The heterocyclic amine modified siloxanes also may be used as surface active agents, including, but not limited to, as surfactants, welling agents and softeners for textiles, flow and leveling agents in coatings, hair care products, skin care and creams for personal care applications and anti-static agents, detergents and softeners for laundry products.

EXAMPLES

Unless otherwise indicated, all parts and percentages are by weight, and are based on the weight at the particular stage of the processing being described.

Example 1

Heterocyclic aminosiloxanes:

The heterocyclic amine modified siloxanes were prepared by the slow addition of the desired heterocyclic amine to a reaction vessel containing heptamethyltrisiloxane modified with allyl glycidyl ether, using 2-propanol (30 wt %) as a solvent. The epoxysiloxane intermediate was

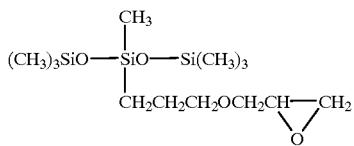

Therefore, 500 g of a trisiloxane, epoxy intermediate, 257.1 g of N-(2-hydroxyethyl) piperazine along with 322.3 g 2-propanol were combined in a roundbottom flask equipped with a reflux condenser and an overhead stirrer. The reaction mixture was slightly exothermic and the flask temperature was allowed slowly to reach a maximum of 90° C. The flask contents were adjusted to 80° C. and held at this temperature for 50 minutes. At this point a perchloric acid titration of the reaction mixture showed that the epoxide content was nil, indicating the reaction was complete. The mixture was filtered through a fine filter pad and stripped on a Rotovap for 1.5 hours at 70° C. and 1.0 mm Hg to afford the desired product, having a Brookfield viscosity of 698 cps (spindle LV-3 @ 100 rpm), and a refractive index of 1.4620 (25° C).

Other compositions of heterocyclic amine modified siloxanes shown below in Table 1 were prepared according to this procedure.

TABLE 1

Description of Heterocyclic amine modified siloxanes $$CH_3-\underset{\underset{CH_3}{|}}{\overset{\overset{CH_3}{|}}{Si}}-O-\left[\underset{\underset{Q}{|}}{\overset{\overset{CH_3}{|}}{Si}}-O\right]_f-\underset{\underset{CH_3}{|}}{\overset{\overset{CH_3}{|}}{Si}}-CH_3$$

Structure of Q Group Type 1

$$C_3H_6OCH_2CH(OH)CH_2N\underset{CH_2CH_2}{\overset{CH_2CH_2}{\diagup\diagdown}}NR$$

General Structure for Q Group Type 2

$$C_3H_6OCH_2CH(OH)CH_2N\underset{CH_2CH_2}{\overset{CH_2CH_2}{\diagup\diagdown}}O$$

| Reference | f | Q Group Type | R Group |
|---|---|---|---|
| HCAS-1 | 1 | 1 | $CH_2CH_2OH$ |
| HCAS-2 | 1 | 1 | $CH_2CH_2OCH_2CH_2OH$ |
| HCAS-3 | 1 | 1 | H |
| HCAS-4 | 1 | 2 | Not Applicable | b. Comparative Silicone Based Surfactant: $Me_3SiO[MeSi(C_3H_6O(C_2H_4O)_8H)O]_1SiMe_3$ (SIL-A) is a comparative TSA. This material was prepared by standard hydrosilation of an allyl terminated polyether with heptamethyltrisiloxane.

c. Comparative Nonsilicone Surfactants:

Table 2 provides descriptions of typical, comparative, nonsilicone surfactants.

TABLE 2

Description of Comparative Conventional Nonsilicone Surfactants

| Reference | Moles EO | Remarks |
|---|---|---|
| OPE | 10 | Octylphenol ethoxylate (TRITON ® X-100) (Union Carbide Corp., Danbury, CT) |
| TAE | 15 | Tallow amine ethoxylate (ETHOMEN ™ T/25) (Akzo Nobel Chemicals Inc.; Chicago, IL) |

Example 2

This example demonstrates the utility of the heterocyclic amine siloxane composition of the present invention as surfactants. Aqueous solutions of these unique compositions provide a significant reduction in surface tension relative to conventional surfactants. Additionally the heterocyclic moiety does not detract from the surface tension lowering associated with traditional TSA (Sil-A). Surface tension was measured using a Cahn microbalance, with a sand blasted platinum blade as the sensor. Solutions of the various components were prepared at 0.1 wt % in 0.005M NaCl water (Deionized), as an equilibrium aid.

TABLE 4

Comparison of Aqueous Surface Tension Properties

| Surfactant | Surface Tension (mN/m) | Composition of Invention |
|---|---|---|
| HCAS-1 | 20 | Yes |
| HCAS-2 | 20 | Yes |
| HCAS-3 + Glacial Acetic Acid (0.037 g) | 21 | Yes |
| HCAS-4 | Insoluble | Yes |
| SIL-A | 21 | No |
| OPE | 29 | No |
| TAE | 41 | No |
| None[b] | 72 | N/A |

[a]Surface tension in mN/m at 25° C.
[b]Surface tension of water from CRC Handbook of Chemistry and Physics: 63 Edition, 1982–1983.

Example 3

The compositions of the present invention provide enhanced spreading similar to the TSAs (SIL-A) and relative to conventional surfactants. When the compositions of the present are insoluble in distilled water, spreading may be achieved by the addition of a small amount of an acid, such as acetic acid, to protonate the amine functionality, thereby increasing water solubility. Additionally if the composition of the invention may be combined with a TSA to achieve enhanced spreading relative to conventional surfactants (Table 3).

Spreading was determined by applying a 10 μL droplet of surfactant solution to a polyester film (3M, IR 1140 transparency film) and measuring the spread diameter after 30 seconds. The solution was applied with an automatic pipette to provide droplets of reproducible volume. Deionized water that was further purified with a Millipore filtration system was used to prepare the surfactant solutions.

| Surfactant | Weight Percent Surfactant | | | | |
|---|---|---|---|---|---|
| | 0.025 | 0.05 | 0.1 | 0.2 | 0.4 |
| HCAS-1 | 22 | 34 | 49 | 45 | 44 |
| HCAS-2 | 18 | 34 | 49 | 52 | 48 |
| HCAS-3 + Sil-A (1:1) | nd | nd | 40 | 47 | 49 |
| HCAS-4 + Sil-A (1:1) | nd | nd | 35 | 46 | 54 |
| Sil-B | 14 | 29 | 44 | 42 | 47 |
| OPE | nd | nd | nd | nd | 8 |

We claim:

1. A composition comprising a heterocyclic amine modified siloxane wherein the heterocyclic amine is a cyclic group of at least four carbon atoms and at least one nitrogen atom, the cyclic group optionally further having one oxygen or sulfur atom or up to two additional nitrogen atoms, and a pesticide.

2. A composition according to claim 1 having the average general formula:

wherein f is between 0 to 50, d=0 to 2, e=0 to 3, g is, if the siloxane is not cyclic, 2+e+2d, or zero if the siloxane is cyclic, d+e+f+g=2 to 50, Q is either $B(O)_j(C_aH_{2a}O)_bRV$ or $R^1$, each a is 2 to 4, each b is 0 to 15, B is a divalent bridging group of C1 to C6, R is a divalent organic group containing 2 to 8 carbons, each optionally OH substituted, $R^1$ is either a polyether or an alkyl radical containing 1 to 18 carbons, j=0 or 1, at least one Q is not $R^1$, and V is a heterocyclic amine monovalent radical of the formula, $-NC_pH_pR^2_p(NR^2)_2$, or $-NC_pH_pR^2_pM_r$, where p=4 to 8, z=0 to 3, r=0 to 3, $R^2$ is hydrogen, a univalent organic group containing 1 to 4 carbons, or $-(C_aH_{2a}O)_hR^3$, where h=1 to 8, $R^3$ is hydrogen, an allyl group of 1 to 4 carbons, or acetyl, and M=oxygen or sulfur.

3. A composition according to claim 1 comprising alternating units of polysiloxane $[XSiO(R^1)_2X]_c$ and a heterocyclic diamine of the general structure $[-NC_pH_pR^2_pN-]$ wherein c=1 to 30, X is $-B(O)_j(C_aH_{2a}O)_bR-$ wherein B is a divalent bridging group, j is 0 or 1, a=2 to 4, b=1 to 12, R is a divalent hydrocarbon group, optionally substituted with a hydroxyl functionality, $R^2$ is hydrogen, a univalent organic group containing 1 to 4 carbons, p=4 to 8 and R1 is either a polyether or an alkyl radical containing 1 to 18 carbons.

4. A compound comprising alternating units of polysiloxane $[XSiO(R^1)_2X]_c$ and a heterocyclic diamine of the general structure $[-NC_pH_pR^2_pN-]$ wherein c=1 to 30, X is $-B(O)_j(C_aH_{2a}O)_bR-$ wherein B is a divalent bridging group, j is 0 or 1, a=2 to 4, b=1 to 12, R is a divalent hydrocarbon group, optionally substituted with a hydroxyl functionality, $R^2$ is hydrogen, a univalent organic group containing 1 to 4 carbons, p=4 to 8 and $R^1$ is either a polyether or an alkyl radical containing 1 to 18 carbons.

5. A composition according to claim 1 additionally comprising a trisiloxane alkoxylate.

6. A composition according to claim 5 additionally comprising an organic cosurfactant.

7. A composition according to claim 2 wherein d=0, e=0 and g=2.

8. A composition according to claim 7 wherein p=4 or 5.

9. A composition according to claim 8 wherein j=1.

10. A composition according to claim 9 wherein one $R^1$ is a polyether, one $R^1$ is Q and the rest are methyl.

11. A composition according to claim 9 wherein all $R^1$ except for one are methyl.

12. A composition according to claim 11 wherein B are $-(CH_2)_2-$, $-(CH_2)_3-$, or $-CH_2CH(OH)CH_2-$.

13. A composition according to claim 11 wherein R groups are selected from the group consisting of $-(CH_2)_2-$, $-(CH_2)_3-$, $-CH_2CH(OH)CH_2-$ and $-CH_2C_6H_9(OH)CH_2-$.

14. A composition according to claim 11 wherein $R^1$ are selected from the group consisting of $-CH_3$, $-C_2H_5$, $-C_2H_2OH$, $(C_2H_4O)_3(C_3H_6O)_2H$; $-(C_2H_4O)_2CH_3$; and $-(C_3H_6O)_3OH$.

15. A composition according to claim 11 wherein f=1.

16. A composition according to claim 15 wherein z=1 and each $R^2$ is hydrogen.

17. A composition according to claim 15 wherein z=0, r=0 and each $R^2$ is hydrogen or univalent organic group of one to four carbon atoms.

18. A composition according to claim 15 wherein z=1 and every $R^2$, except on the nitrogen is hydrogen and $R^2$ on the nitrogen is a polyether.

19. A composition according to claim 15 wherein r=1 and M=0.

20. A process comprising adding a composition according to claim 1 to agricultural crops.

21. A compound comprising a heterocyclic amine modified siloxane having the average general formula:

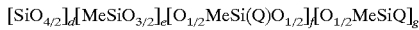

wherein f is between 0 to 50, d=0 to 2, e=0 to 3, g is, if the siloxane is not cyclic, 2+e+2d, or zero if the siloxane is cyclic, d+e+f+g=2 to 50, Q is either $B(O)_j(C_aH_{2a}O)_bRV$ or $R^1$, each a is 2 to 4, each b is 0 to 15, B is a divalent bridging group of C1 to C6, R is a divalent organic group containing 2 to 8 carbons, each optionally OH substituted, $R^1$ is either a polyether or an alkyl radical containing 1 to 18 carbons, j=0 or 1, at least one Q is not $R^1$, and V is a heterocyclic amine monovalent radical of the formula, $-NC_pH_{2p}(NR^2)_e$, where p=4, z=1, $R^2$ is a polyether group of the formula $-(C_aH_{2a}O)_hR^3$, where h=2 to 8, and $R^3$ is hydrogen, an alkyl group of 1 to 4 carbons, or acetyl.

* * * * *